United States Patent [19]

Weth

[11] Patent Number: 5,589,499
[45] Date of Patent: Dec. 31, 1996

US005589499A

[54] DOPAMINERGIC AGENTS FOR THE TREATMENT OF CEREBRAL AND PERIPHERAL BLOOD FLOW DISORDERS

[76] Inventor: Gosbert Weth, Coburgerstrasse 6, W-8520, Erlangen, Germany

[21] Appl. No.: 339,423

[22] Filed: Nov. 14, 1994

Related U.S. Application Data

[63] Continuation of Ser. No. 981,368, Nov. 25, 1992, abandoned.

[51] Int. Cl.$^6$ ................................................ A61K 31/40
[52] U.S. Cl. ................................. 514/423; 514/428
[58] Field of Search .................................... 514/423, 428

[56] References Cited

U.S. PATENT DOCUMENTS

| | | | |
|---|---|---|---|
| 4,046,889 | 9/1977 | Ondetti et al. | 424/244 |
| 4,316,906 | 2/1982 | Ondetti | 424/274 |
| 4,374,829 | 2/1983 | Harris et al. | 424/177 |

FOREIGN PATENT DOCUMENTS

| | | |
|---|---|---|
| 0491061 | 6/1992 | European Pat. Off. . |
| 0498899 | 8/1992 | European Pat. Off. . |
| 3932749 | 4/1991 | Germany . |
| 4016941 | 11/1991 | Germany . |

OTHER PUBLICATIONS

C. Hansch (Ed.) Comprehensive Medicinal Chemistry, vol. 2, Pergamon Press, Oxford, 1990, pp. 400 to 404.
The Merck Index, 10. ed., 1983, pp. 1174 to 1175, No. 8039 to 8042.
J. Witzke and H.–J. Gilfrich, Deutsche Apotheker Zeitung 127. Jahrg., NR. 38, 17.09.1987, pp. 103 to 105.
J. Fuchs, et al, "2 Mercaptopropronylglycine . . . Damage", Arzneim–Forsch/Drug Res. 35(11), Nr9 (1985).
H. Yamauchi, et al., "General Pharmacological . . . Rentiapril", Arzneim–Forsch/Drug Res. 37(1), Nr2 (1987).
Toyohazw Takada, et al. "Effects of an Angiotensin . . . Dogs", Short Communications, Japan. J. Pharmacol. 38,227 (1985).
Yoshio Suzuki, et al. "Studies on Mechanisms of Antinephritu Action of SA–446", Japan. J. Pharmacol. 42, 465–475 (1986).
C. Lombardi, et al. Enalapril . . . patients, "Journal of Biological Regulators & Homeostatic Agents," Band 3, Nr 3, Jul.–Sep. 1989, Seiten 128–129, Milano, Italy.
C. Lombardi, et al., "Meicanismi . . . ipofisario", Minerva Medus, Band 81, Nr 9, Sep. 1990 Seiten 587–590, IT.
J. E. F. Reynolds, et al. "Martindale the Extra Pharmacopoeia", Ed. 29, 1989, The Pharmaceutical Press, Seiken 478–480, London, GB.
J. E. F. Reynolds, et al. "Martindale, The Extra Pharmaceopoeia", Ed. 29, 1989, The Pharmaceutical Press, Seiken 493, London, G.B.
W. B. Malarkey, et al. "Angioteusin . . . manner", The Journal of Clinical Endocrinology & Metabolism, Bd 64, Nr 4, Apr. 1987, pp. 713–717, The Endocrins Society.
Angiology, Band 41, NR. 5, May 1990, pp. 377–381, New York, US. I. Saito et al.: "Effect of Captopril On Plasma Prolactin In Hypertension"—Summary: p. 379, Figure 1.
Prolactin, Basic And Clinical Correlates, Band 1, 1985, pp. 53–57, Liviana Press, Padova, IT; C. Denef: "Paracrine Interaction In Anterior Pituitary" —Entire Document.
The Journal of Clinical Endocrinology & Metabolism, Band 64, NR.4, Apr. 1987, pp. 713–717, The Endocrine Society, US: W. B. Malarkey et al.: "Angiotensin II Promotes Prolactin".
"Release From Normal Human Anterior Pituitary Cell Culters in a Calcium–Dependent Manner" 1987.
The Merck Index, Published by Merck & Co Inc, Rahway N.J. Eleventh Edition No. 3521, pp. 557–558 (1989).
Merck Index, 11th Edition, (1989), Merck & Co., Inc., Rahway N.J. p. 8149.

Primary Examiner—Theodore J. Criares
Attorney, Agent, or Firm—Ladas & Parry

[57] ABSTRACT

The invention deals with the use of N-(aminoacyl)-amino acids of Formula (I), especially anapril, (2 R, 4 R)-2-(2-hydroxy-phenyl)-3-(3-aminopropionyl)-4-thiazolidine carboxylic acid, and 1-[(2 S)-3-amino-4-methyl-propionyl]-2-proline as dopaminergic active ingredients for increasing central or peripheral blood flow disorders.

4 Claims, 1 Drawing Sheet

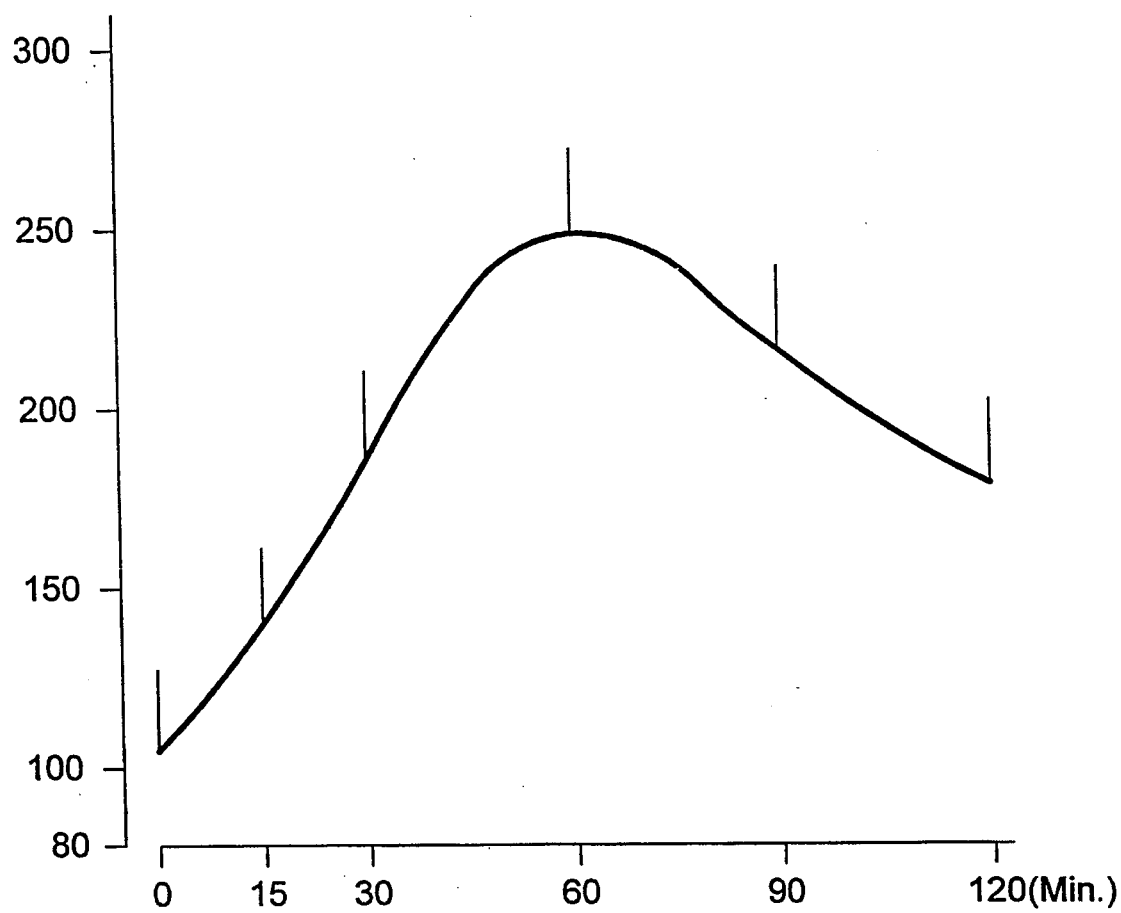

DOPAMINERGIC AGENTS FOR THE TREATMENT OF CEREBRAL AND PERIPHERAL BLOOD FLOW DISORDERS

This is a continuation of application Ser. No. 07/981,368 filed on Nov. 25, 1992, now abandoned.

FIELD OF THE INVENTION

The invention relates to dopaminergic agents for the treatment of disorders of cerebral and peripheral blood flow.

BACKGROUND OF THE TECHNICAL FIELD

As the inventor has determined, N-aminoacyl)amino acids, on the basis of their release of dopamine, lead to increased blood flow, both centrally and peripherally. Up till now agents belonging to the group of N-(aminoacyl)amino acids (known as angiotensin-converting enzyme inhibitors or ACE-inhibitors) have been used as drugs for lowering blood pressure.

An increased noradrenaline content contributes to high blood pressure. It is known that ACE-inhibitors lower blood pressure by inhibiting the formation of angiotensin II. In this connection some experts discuss a small reduction of the noradrenaline. Noradrenaline, however, is formed from dopamine and therefore hitherto one had to expect that in any reduction of noradrenaline there would also be a lowering of dopamine.

In tests of the inventor it has now been unexpectedly established that the opposite occurs: when administering N-(aminoacyl)amino acids, a highly significant rise of dopamine occurs. On the basis of this release of dopamine (dopaminergic effect), the administration of the above noted compounds leads to a cerebral and peripheral increase of blood flow; this is surprising against the known background.

It is known that in the case of blood flow disorders in patients having low blood pressure, dopamine can be used for stabilizing blood circulation. The tests of the inventor show that by using N-(aminoacyl)-amino acids with patients used in the present tests who have low blood pressure, there is no further lowering of the blood pressure; instead, there is an increased central and peripheral blood flow.

This effect can be detected cerebrally: the dopaminergic action is identifiable and demonstrable in the brain by means of neurotransmitter changes according to the method developed by the inventor (Dr. G Weth, "Das Verhalten der Neurotransmitter . . . " [The Behavior of Neurotransmitters . . . ], a dissertation, University of Würzburg 1987, pages 123–138). Tests on patients to whom N-(aminoacyl)-amino acids had been administered sublingually showed a centrally detectable dopaminergic effect.

An increase of blood flow with N-(mercaptoacyl)-amino acids is known from the DE-OS 39 32 749 (published on Apr. 11, 1991) and from the EP-A 498 899 (published on Aug. 19, 1992), both in the name of the present inventor. These compounds, however, have a different structure from the N-(aminoacyl)-amino acids used according to the present invention.

Moreover, the effect of ACE-inhibitors in respect of lowering prolactin in the plasma has been described in various works. These works and literature passages of which the inventor has further become aware are as follows: Journal of Biological Regulators and Homeostatic Agents, Volume 3, No. 3, July–September 1989, pages 128–129, Milano, IT, C. Lombardi et al; Minerva Medica, Volume 81, No. 9, September 1990, pages 587–590, IT, C. Lombardi et al; J.E.F. Reynolds et al: Martindale, the Extra Pharmacopoeia, Ed. 29, 1989, the Pharmaceutical Press, pages 478–480, London, GB, Summary 12969-e: enalapril maleate; J.E.F. Reynolds et al: Martindale, the Extra Pharmacopoeia, Ed. 29, 1989, the Pharmaceutical Press, page 493, London, GB, Summary 729-s: perindopril; The Journal of Clinical Endocrinology & Metabolism, Volume 64, No. 4, April 1987, pages 713–717, The Endocrine Society, U.S., W. B. Malarkey et al.; Angiology, Volume 41, No. 5, May 1990, pages 377–381, New York, U.S., I. Saito et al, Summary, page 379, Figure 1; Prolactin, Basic and Clinical Correlates, Volume 1, 1985, pages 53–57, Liviana Press, Padova, IT, C. Denef; J.E.F. Reynolds et al., publisher Martindale, the Extra Pharmacopoeia, Ed. 29, 1989, pages 468–472, London, GB, paragraph 856-C: captopril; Fuchs, J. et al.: 2-Mercapto-propionylglycine and Related Compounds in Treatment of Mitochondrial Dysfunction and Postichemic Myocardial Damage in: Arzneim.-Forsch./Drug Research 35 (II), No. 9, 1985, pages 1394–1402; Yambuchi, H. et al.: General Pharmacological Properties of the Potent Angiotensin Converting Enzyme Inhibitor Rentiapril, in: Arzneim.-Forsch./Drug Res. 37 (I), No. 2, 1987, pages 157–164; Takada, Toyokazu et al.: Effects of an Angiotensin I-Converting Enzyme Inhibitor (SA-446) on Renal Function on Dogs, in: Japan J. Pharmacol. 38, 1985, pages 227–230; Studies on Mechanisms of Antinephritic Action of SA-445, an Angiotensin I Converting Enzyme Inhibitor (1) a comparison with Actions of Spironolactone, Kallidionogenase and Saralacin, in: Japanese J. Parmacol. 42, 1986, pages 465–475; U.S. Pat. Nos. 4,046,889; 4,316,906, EP-A-366 033.

The tests indicated hereinafter show that an effect of clearly increasing blood flow occurs due to administering N-(aminoacyl)-amino acids.

An increase of blood flow was demonstrated in a video-film. It is possible to show by means of a video-film that after administering the substances described hereinafter, there occurs a distinct increase, of more than 50%, of blood flow. Additionally, it is shown that also in the case of decreased blood flow (either caused by drugs or by atherosclerosis), there occurs an obvious (up to a five-fold) increase within one minute after an intravenous administration of these substances.

DETAILED DESCRIPTION OF THE INVENTION

The subject matter of the invention is the use of N-(aminoacyl)-amino acids and salts thereof as dopaminergic additives for the treatment of cerebral and peripheral blood flow disorders. Said N-(aminoacyl)-amino acids are those of the general Formula (I):

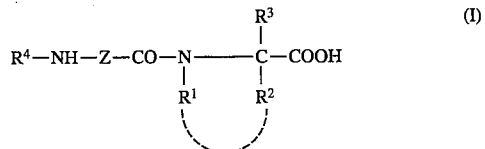

wherein $R^1$ is hydrogen or lower alkyl;

$R^2$ is hydrogen, lower alkyl, phenyl, aralkyl, imidazolylalkyl or indolyl-alkyl, which can be substituted by lower alkyl, hydroxy, hydroxyalkyl, methylenedioxy, mercapto, mercaptoalkyl, amino, guanidino or carboxy, or $R^1$ and $R^2$ (as shown by the broken line) together are a pyrrolidine, piperidine, or a thiazolidine ring, or such rings condensed as tetrahydroisoquinolyl, octahydroindolyl, or octahydrocyclopenta[b]pyrrolyl, which rings can be substituted by one or more lower alkyl, aralkyl, phenyl, furyl, thienyl, pyridyl or naphthyl, which substituents can themselves be substituted by one or more lower alkyl, hydroxy-lower-alkyl, mercapto-lower-alkyl, hydroxy, lower-alkoxy, alkylenedioxy, halogen, nitro, amino, lower-alkylamino or acylamino;

$R^3$ is hydrogen or methyl;

$R^4$ is hydrogen, alkyl or the group

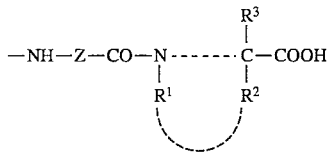

wherein $R^1$, $R^2$ and $R^3$ are as defined above, and Z is as defined below, and wherein when $R^4$ is an alkyl group, it can be substituted by one or more aromatic groups (especially phenyl), amino groups, hydroxyl groups, carboxy groups, and carbo(lower)alkoxy groups, and Z is a straight-chain or branched-chain alkylene having from 1 to 3 carbon atoms;

or salts thereof.

In a preferred class of compounds of Formula I $R^4$ is hydrogen or

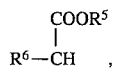

where $R^5$ is hydrogen or lower alkyl and $R^6$ is 2-phenylethyl or n-propyl.

The aforestated term "lower alkyl" alone or in combination with other groups is preferably a $C_1-C_4$ alkyl group. The term "lower-alkoxy" is preferably a $C_1-C_4$ alkoxy group.

"Aralkyl" is preferably a phenyl($C_1-C_6$ alkyl) group,

"Alkyl" (alone or in combination with other groups) is preferably a $C_1-C_6$ alkyl group.

"Halogen" is preferably chlorine, bromine and iodine.

"Acylamino" is preferably a $C_1-C_4$ acylamino group.

Salts of the compounds of Formula (I) are preferably those with pharmaceutically compatible organic or inorganic acids, or with pharmaceutically compatible organic or inorganic bases. As examples of such acids, one should mention maleic acid and hydrochloric acid. Examples of bases are sodium, calcium, and magnesium hydroxide.

For purposes of the present invention, the following compounds used are especially preferred:

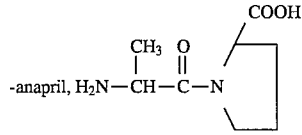

preferred in the form of a maleate;

(2 R, 4 R)-2-(2-hydroxy-phenyl)-3-(3-aminopropionyl)-4-thiazolidine carboxylic acid;

1-[(2 S)-3-amino-$C_1-C_4$-alkylpropionyl]-2-proline;

1-[(2 S)-3-amino-2-methyl-propionyl]-2-proline];

enalapril, preferred in the form of a hydrogen maleate;

perindopril.

The compounds indicated are known products, and those skilled in the art are generally familiar with their production.

The dispensing of said active ingredients takes place in general in a dosage of 2 to 20 mg per day, preferably in a dosage of about 20 mg per day. The administration can be oral, parenteral, or sublingual, wherein the sublingual mode of administration is preferred.

The indicated active ingredients can be used as such or in the form of conventional pharmaceutical formulations, especially in the form of tablets, granules, or preparations for injections, on the basis of carriers and adjuvants known in the medical art.

Examples of such carriers and adjuvants are: lactose, stearic acid, sodium bicarbonate, corn starch, magnesium stearate, coloring substances (e.g. E 127, 131, 171, 172), $CaCO_3$, and magnesium orotate. Suitable pharmaceutical formulations are, for example, tablets containing the additive in the following amounts: 5 mg anapril maleate, 10 mg enalapril or 4 mg perindopril-ter.-butylamine salt. Pharmaceutical formulations in the form of granules contain the active ingredient, in an amount of 5 mg, for example. Injection solutions contain the additive in an amount of 2 mg, for example.

Further active ingredients which can be used in the invention are: quinapril, lisinopril, and ramipil. Pharmaceutical formulations in the form of tablets may contain these substances, e.g. in the following amounts: 5 mg or 10 mg or 20 mg quinapril; 2,5 or 10 mg lisinopril; 1,25 mg ramipil.

The dopaminergic effect is demonstrated by means of the following pharmacological test.

Pharmacological Test

The utilized N-(aminoacyl)-amino acid anapril-hydrogenmaleate (compound A) leads to an increased release of dopamine.

Experimental Method (Procedure)

2×12 patients (aged 75±10), who suffered from peripheral as well as central blood flow disorders, were selected for the tests. Prior to the dose of anapril and also 15, 30, 60, 90, and 120 minutes after the dose of anapril dopamine was determined for these patients. It appeared that in the case of these patients there occurred a highly significant increase of dopamine after 15 minutes. The patients were administered sublingually 20 mg of compound A. (The blood pressure was between 100/70 and 170/110; the mean value (MV) was 130/90 mmHg).

Experimental Result

FIG. 1/1 demonstrates the fact that after dispensing 20 mg of anaprilhydrogen maleate per patient (average weight 60 kg, dispensed sublingually), there occurs a release of dopamine.

Brief Explanation of the Drawing

The single figure shows the time slope of the dopamine release. From this figure it becomes evident that even after 15 minutes there takes place a significant increase of dopamine, which culminates after about 60 minutes, and then further continuously decreases.

The dopamine values were determined in the following way: at the aforestated time intervals the patients were drawn 5 ml blood each, and the blood was transmitted to especially prepared vacuum containers which contained glutathione and EDTA (ethylenediaminetetraacetic acid). The blood was immediately cooled to 2 degrees and centrifuged at 2 degrees. The excess (blood plasma) was deep-frozen at −80° C. until dopamine was evaluated.

The dopamine evaluation was carried out as described in the aforementioned dissertation of the inventor, Dr. G. Weth.

The dimensional data for dopamine are given in pg/ml.

| | Statistical Evaluation after a Dose of 20 mg Anapril-Hydrogenmaleate | | | | |
|---|---|---|---|---|---|
| Dopamine | Time | MV (pg/ml) | Disp. | N | P (T) |
| Dop. | 0 | 105 | 67 | 12 | |
| Dop. | 15 | 143 | 78 | 12 | p <0.05 |
| Dop. | 0 | 105 | 67 | 12 | |
| Dop. | 30 | 188 | 72 | 12 | p <0.001 |
| Dop. | 0 | 105 | 67 | 12 | |
| Dop. | 60 | 253 | 81 | 12 | p <0.001 |
| Dop. | 0 | 105 | 67 | 12 | |
| Dop. | 90 | 230 | 62 | 12 | p <0.001 |
| Dop. | 0 | 105 | 67 | 12 | |
| Dop. | 120 | 182 | 53 | 12 | p <0.001 |

A statistical evaluation of the dopamine values shows that 30 minutes after dispending 20 mg of compound A, there is attained a highly significant increase of dopamine.
(MV—mean value; Disp.=dispersion; N=number of patients; P (T)=significance for p<0.05).

I claim:

1. A method for increasing the rate of cerebral or peripheral blood flow in a patient who already suffers from cerebral or peripheral blood flow disorders which comprises administering to such a patient an amount of a compound effective to increase the flow of blood in said patient and to cause a significant increase of dopamine in said patient, wherein said compound is of the Formula (I):

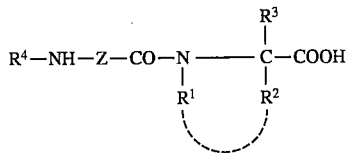

wherein $R^1$ and $R^2$ (as shown by the broken line) together are a pyrrolidine ring;

$R^3$ is hydrogen;

$R^4$ is hydrogen, alkyl or

where $R^5$ is hydrogen or lower alkyl and $R^6$ is 2-phenylethyl or n-propyl, and Z is a straight-chain or branched-chain alkylene having from 1 to 3 carbon atoms, or a pharmaceutically acceptable salt thereof, wherein the compound is administered to the patient at a dosage of 2 to 20 mg per day.

2. A method according to claim 1 which includes determining the level of dopamine in the patient prior to administering the compound of Formula (I) and again determining the level of dopamine in the patient several minutes after administration of said compound to determine whether there results a highly significant increase of dopamine.

3. A method according to claim 1, in which the compound of Formula I is

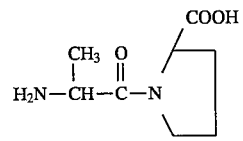

or a pharmaceutically acceptable salt thereof.

4. A method according to claim 3, in which the maleate salt is used.

* * * * *